United States Patent [19]

Tuda et al.

[11] 4,273,959
[45] Jun. 16, 1981

[54] LARYNX STROBOSCOPE DEVICE

[75] Inventors: Koji Tuda, Tokyo; Hironobu Nagashima; Masatoshi Marui, both of Kami Fukuoka, all of Japan

[73] Assignee: Asahi Kogaku Kogyo Kabushiki Kaisha, Tokyo, Japan

[21] Appl. No.: 960,544

[22] Filed: Nov. 14, 1978

[30] Foreign Application Priority Data

Nov. 14, 1977 [JP] Japan .................................. 52-136434

[51] Int. Cl.$^3$ .............................................. G10L 1/02
[52] U.S. Cl. ................................................. 179/1 SC
[58] Field of Search .................... 73/587, 645, 657; 128/630, 1 R; 179/1 R, 1 SP, 1 SC; 84/464 R

[56] References Cited

U.S. PATENT DOCUMENTS

| 3,026,449 | 3/1962 | Rappaport | 179/1 SP |
| 3,203,254 | 8/1965 | Thomas et al. | 73/466 |
| 3,247,710 | 4/1966 | Thomas et al. | 73/466 |

Primary Examiner—Charles E. Atkinson
Assistant Examiner—E. S. Kemeny
Attorney, Agent, or Firm—Sughrue, Rothwell, Mion, Zinn and Macpeak

[57] ABSTRACT

A stroboscope device for diagnosis of larynx emissions. The system uses a saw tooth wave for generating in synchronization with a vocal cord vibration saw tooth waves whose voltages are constant in minimum and maximum values. A reference voltage generating circuit is used whose output voltage is variable and a discharge tube light emission control signal generating circuit compares the instantaneous voltage of each saw tooth wave with the output of the reference voltage generating circuit to generate a discharge tube light emission control signal in a phase shift range with respect to said vocal cord vibration. The discharge tube light emission control signal may be generated in a desired phase of said vocal cord vibration every period of said vocal cord vibration or at a repetition rate of multiple periods of the vocal cord vibration.

14 Claims, 35 Drawing Figures

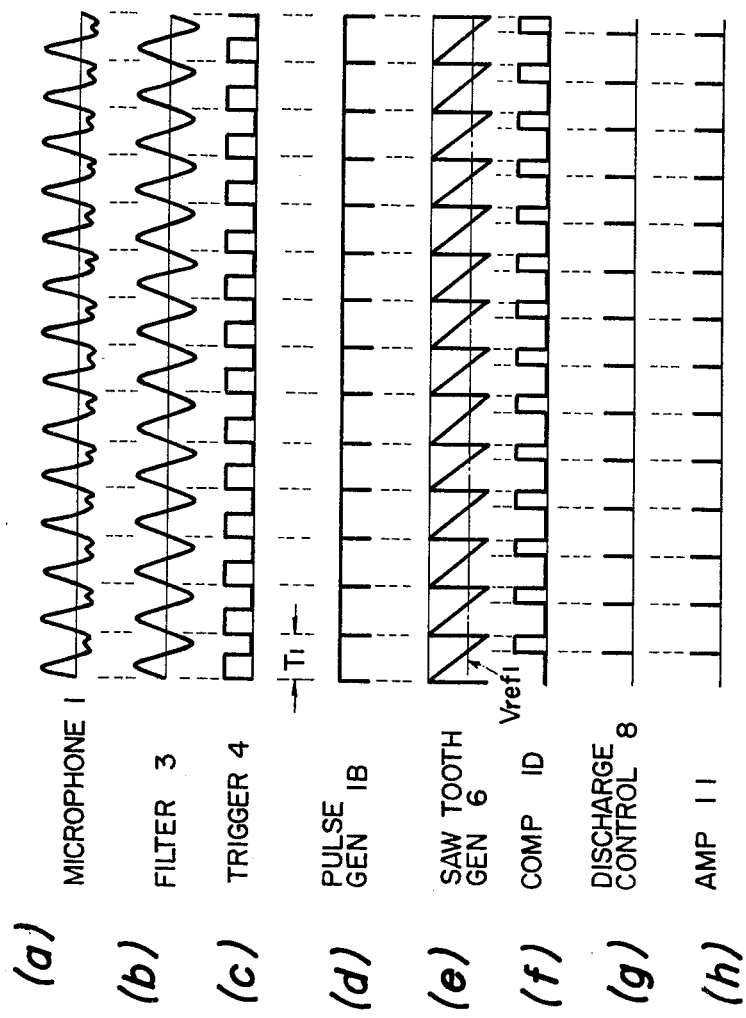

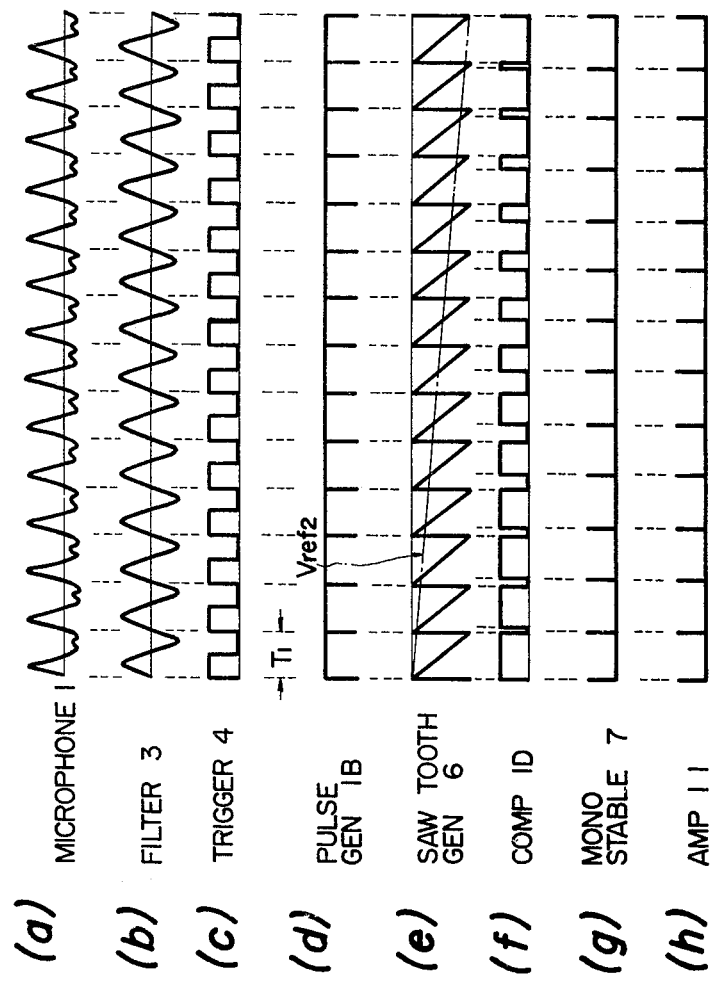

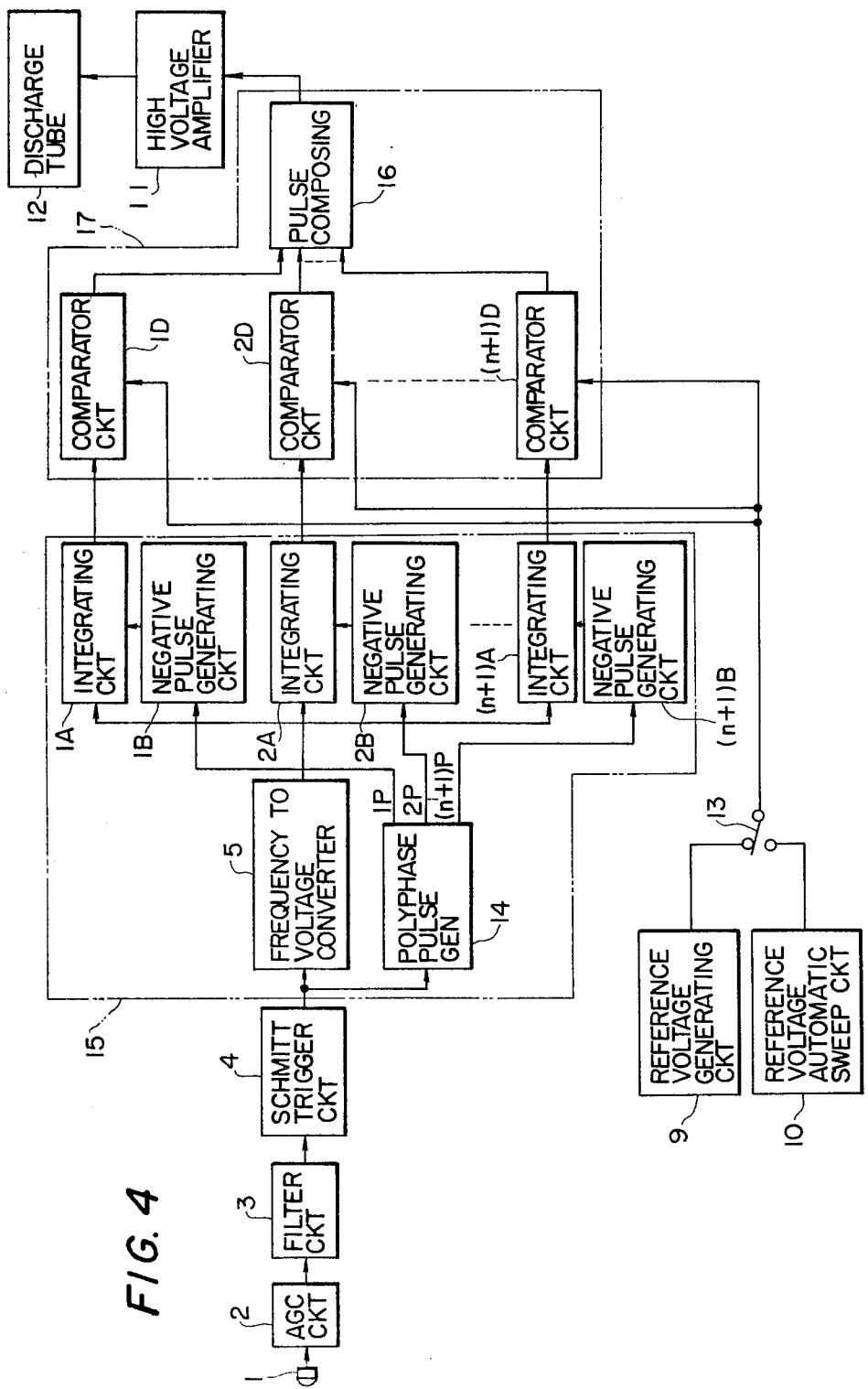

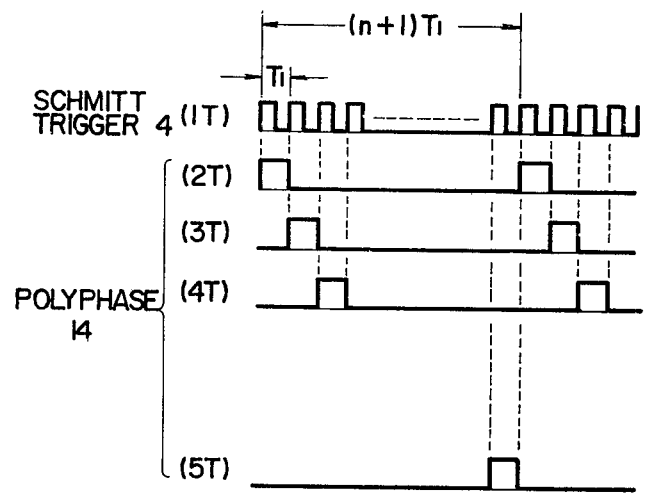
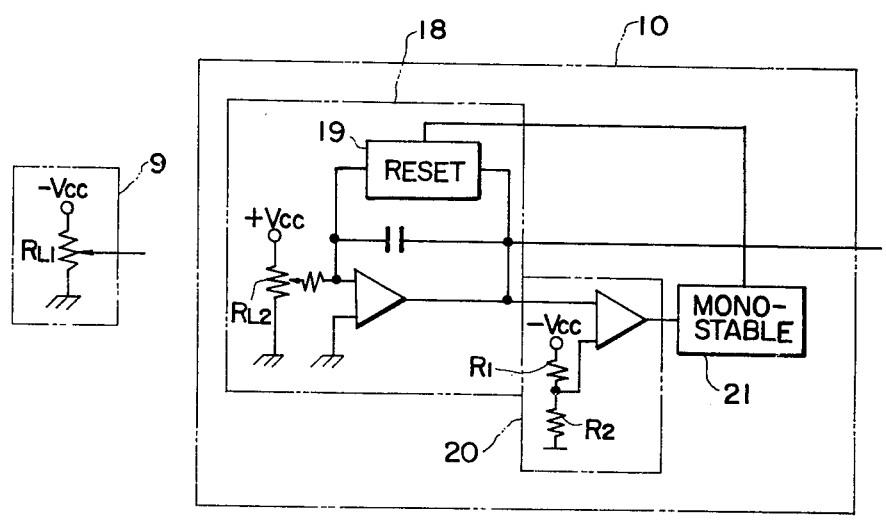

LARYNX STROBOSCOPE DEVICE

BACKGROUND OF THE INVENTION

This invention relates to a larynx stroboscope device for observing and diagnosing vocal cords which make voice emissions. As is well known in the art, a larynx stroboscope is a device that operates to cause a discharge tube to emit light in synchronization with the vibration of the vocal cords which are making voice emissions and to apply the light to the vocal cords. Hence, the observer can observe the vocal cords as if they were at rest. In addition, the observer can observe the stationary image of the vocal cords in different desired phases thereof by changing the discharge tube light emission phase with respect to vocal cord vibration.

Furthermore, it is also possible to observe the vocal cords gradually moving, or the vocal cords in slow motion, by automatically, continuously and gradually changing the phase. Hereinafter, where the discharge tube emits light in phase with vocal cord vibrations, the range in which the phase can change will be referred to as "a phase shift range" when applicable.

A conventional larynx stroboscope device is disadvantageous in that the phase shift range can greatly change depending on the frequency of the vocal cord vibration. For instance, where the phase is changed by operating a foot-operated pedal, the phase is changed considerably by slightly changing the amount of pressure on the pedal when the vocal cord vibration frequency is high, when compared with the case where the vocal cord vibration frequency is low. Accordingly, it is difficult to precisely observe the vocal cords when the vocal cord vibration frequency is high.

Furthermore, with the conventional larynx stroboscope device, when the observer observes the vocal cords in slow motion, the phase shift range with respect to the vocal cord vibration obtained when the vocal cord vibration frequency is low is very different from that obtained when the vocal cord vibration frequency is high. The time required for the phase to complete its change in the phase shift range is independent of the vocal cord vibration frequency. Therefore, if a rate at which the phase changes is referred to as "a phase shift rate", then the phase shift rate changes depending on the vocal cord vibration frequency. In other words, if the vocal cord vibration frequency of a person to be examined is changed when his vocal cords are observed in slow motion, the speed of the slow motion is accordingly, changed, and therefore it is difficult to observe the vocal cords.

SUMMARY OF THE INVENTION

Accordingly, an object of this invention is to provide a larynx stroboscope device in which all of the above-described drawbacks accompanying a conventional larynx stroboscope device are eliminated in order to precisely observe vocal cords.

These and other objects are accomplished by means of a novel larynx stroboscope system having the following important facets.

With the larynx stroboscope according to the invention, the phase shift range is independent of the vocal cord vibration frequency, and therefore it is possible to observe the vocal cords in a stable state. It is also possible to observe the image of the vocal cords in a desired phase readily and precisely irrespective of the vocal cord vibration frequency. For instance, in the case where the phase is changed by operating a foot-operated pedal, the phase shift range corresponding to the full-stroke of the foot-operated pedal is maintained unchanged even if the vocal cord vibration frequency is changed. Accordingly, the same amount of phase shift is obtained for the same amount of variation in pressure on the pedal. Thus, the device according to the invention overcomes the drawback in the prior art where it is difficult to control the phase because of the variations of the vocal cord vibration frequency.

According to the invention, it is possible to observe the vocal cords in slow motion with the phase shift rate independent of the vocal cord vibration frequency. In general, the vibration frequency of vocal cords making voice emissions is varied, and it is especially difficult to maintain a constant vibration frequency of the vocal cords of a patient. However, according to the invention, it is possible to observe vocal cords in a slow motion state irrespective of the vocal cord vibration frequency and accordingly problems in the vocal cords can be precisely diagnosed.

According to the invention, the instantaneous voltage of a saw tooth wave is produced in synchronization with a vocal cord vibration and whose voltage's minimum and maximum values are constant independent of the vocal cord vibration frequency. This waveform is compared with the output of a reference voltage generating circuit whose output voltage is variable or the output voltage of a reference voltage automatic sweep circuit whose output voltage changes automatically and continuously. Hence the image of the vocal cords is observed in a desired phase or in a slow motion state. In this operation, the phase of the vocal cords being observed can be detected from the output of the reference voltage generating circuit or of the reference voltage automatic sweep circuit independently of the vocal cord vibration frequency. Therefore, if the output of the reference voltage generating circuit or the reference voltage automatic sweep circuit is used to drive a meter or the like, the phase can be determined from the indication of that indicator. Accordingly, if the vocal cord image is subjected to comparison observation in different phases, the phase difference between these vocal cord images can be known, which contributes greatly to the analysis of the vocal cords.

This invention will be described with reference to the drawings and the preferred embodiments as follows.

BRIEF DESCRIPTION OF THE DRAWINGS

FIG. 2 (comprising a–h) is a diagram showing one example of waveforms at various parts in the circuitry shown in FIG. 1;

FIG. 3 (comprising a–h) is also a diagram showing one example of waveforms at various parts in the circuitry shown in FIG. 1;

FIG. 4 is a block diagram showing the circuitry of a second example of the larynx stroboscope according to the invention;

FIG. 5 is a waveform diagram showing the relationships between the input and output waveforms of a polyphase pulse generating circuit;

FIG. 7 is a block diagram showing one example of a reference voltage generating circuit and a reference voltage automatic sweep circuit;

DESCRIPTION OF THE PREFERRED EMBODIMENT

Figure 1:
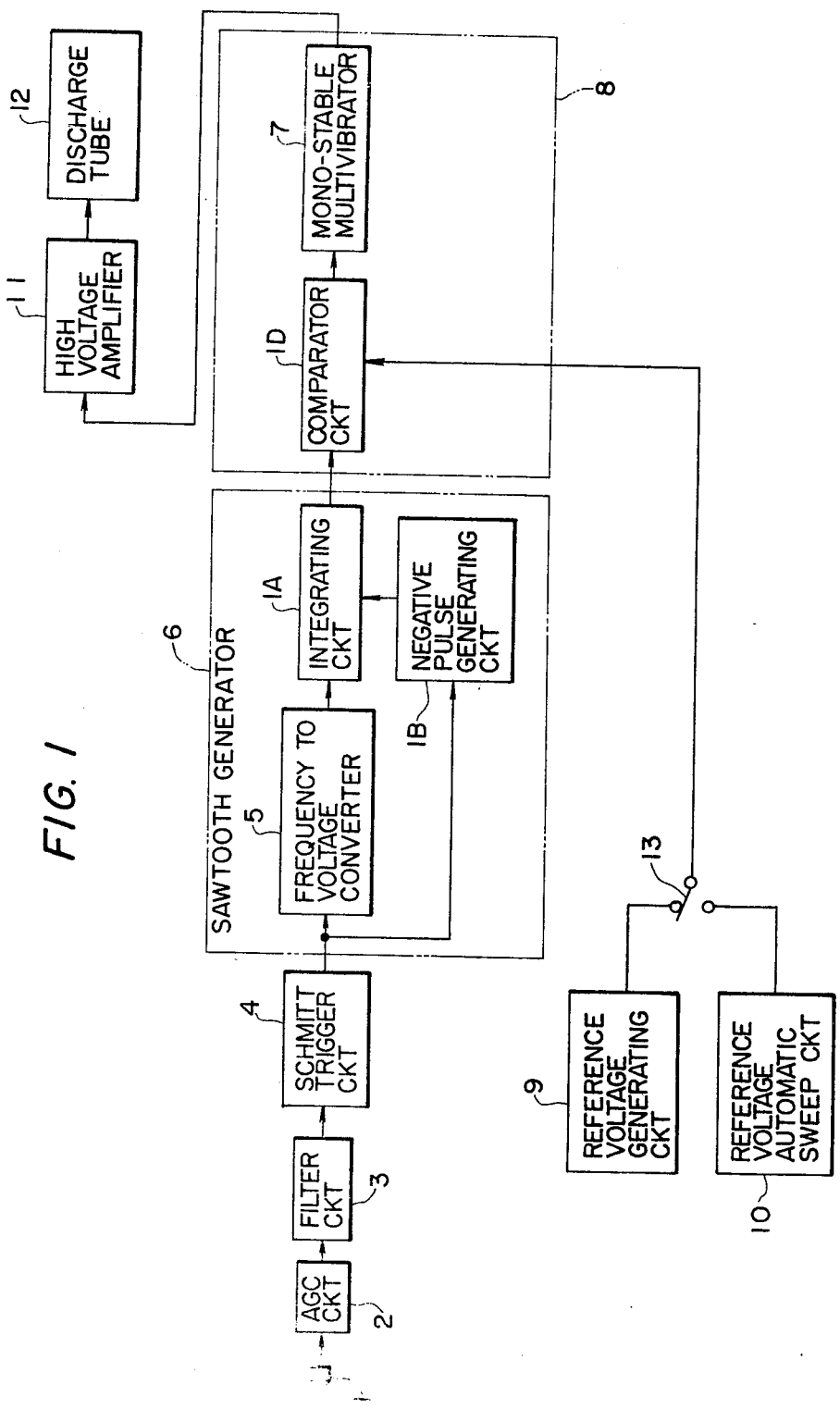
FIG. 1 is a block diagram showing the circuitry of one example of a larynx stroboscope according to this invention.

One embodiment of this invention will now be described with reference to the accompanying drawings. FIG. 1 is a block diagram showing a circuit which detects vocal cord vibration and provides a discharge tube light emission control signal in a desired phase of the vocal cord vibration or in a phase which changes automatically and continuously with respect to the vocal cord vibration. The circuit comprises a contact microphone 1 used as the sensor. An AGC circuit 2 receives sensor output and transmits it to a filter circuit block 3. A Schmitt trigger circuit 4 is coupled to the filter 3. A frequency-to-voltage converter 5, an integrating circuit 1A and a negative pulse generating circuit 1B, form a saw tooth wave generating circuit 6.

A comparator circuit 1D and a mono-stable multivibrator 7 form a xenon discharge tube light emission control signal generating circuit 8. A reference voltage generating circuit 9 and a reference voltage automatic sweep circuit 10 are coupled to a change-over switch 13. The output side comprises a high voltage amplifier 11 and a discharge tube 12.

FIG. 2 shows waveforms at various portions of FIG. 1. Waveform (a) shows one example of a vocal cord vibration waveform detected by the contact microphone. Waveform (b) is the output of the filter circuit block 3. Waveform (c) is the output of the Schmitt trigger circuit 4. The output of the negative pulse generating circuit 1B is waveform (d) and (e) is the output of the saw tooth wave generating circuit 6. Waveform (f) is the output of the comparator circuit 1D and waveform (g) is the output of the discharge tube light emission control signal generating circuit 8. Finally, waveform (h) is the output of the high voltage amplifier circuit 11.

In operation, contact microphone 1 is placed on the throat of a patient adjacent the larynx to detect the vibration signal of the vocal cords making voice emissions. One example of the vocal cord vibration waveform is as shown in waveform (a) of FIG. 2. The magnitude of vocal cord vibration is highly variable with individuals and is varied during sound emissions. Therefore, in order to obtain a stable output, the output of the contact microphone 1 is applied to the AGC circuit 2. If light emission from the discharge tube is not in synchronization with the repetitive period of the vocal cord vibration, the image of the vocal cords being observed becomes irregular, in the larynx stroboscope.

Therefore, the output of the AGC circuit 2 is applied to the filter circuit block 3, whereby the fundamental wave (the repetitive frequency of the vocal cord vibration) of the waveform is obtained as shown in waveform (b) of FIG. 2. This output is converted into a square wave having a frequency equal to the vocal cord vibration frequency as shown in waveform (c) of FIG. 2, with the aid of the Schmitt trigger circuit 4.

The negative pulse generating circuit 1B operates to generate a negative pulse (as shown in the part (d) of FIG. 2) which is equal in frequency to the square wave generated by the Schmitt trigger circuit 4. The negative pulse is synchronous with the rise of the square wave, and has a pulse width which is so short that it can be disregarded when compared with the period of the square wave. The square wave output of the Schmitt trigger circuit 4 is employed as the input signal to the negative pulse generating circuit 1B and as the input signal to the frequency-to-voltage converter circuit 5. The frequency-to-voltage converter circuit 5 (hereinafter referred to as "an F-V converter circuit 5" when applicable) generates a DC voltage output directly proportional to the frequency of the square wave output of the Schmitt trigger circuit 5. The output of the F-V converter circuit 5 is applied to the integrating circuit 1A that is reset by the negative output pulse of the negative pulse generating circuit 1B. Thus, a saw tooth wave as shown in the part (e) of FIG. 2 in synchronization with the vocal cord vibration frequency and having the same frequency as the vocal cord vibration frequency, can be obtained. This saw tooth wave is the output of the saw tooth wave generating circuit 6 made up of the integrating circuit 1A and the negative pulse generating circuit 1B. The minimum and maximum values of the saw tooth wave (e) thus obtained are constant irrespective of frequencies. The reason for this is as follows:

If it is assumed that the frequency of the square wave output of the Schmitt trigger circuit 4 is represented by f, then the output voltage $V_f$ of the F-V converter circuit 5 is:

$V_f = K_1 f$ (where $K_1$ is a constant).

If voltage $V_f$ is applied to the integrating circuit 1A, then the output $V_t$ of the integrating circuit 1A can be represented by the following equation:

$$V_t = K_2 \int V_f dt$$

$$= K_2 \int K_1 f dt \text{ (where } K_2 \text{ is a constant)}$$

As was described before, the negative pulse generating circuit 1B generates a negative pulse which is equal in frequency to the square wave outputted by the Schmitt trigger circuit 4. This negative pulse is synchronous with the rise of the square wave and has a pulse width $T_2$ which is so short that it can be disregarded when compared with the period $T_1$ of the square wave. By this negative pulse, the output of the integrating circuit 1A is reset. In this case, the output $V_t$ of the integrating circuit 1A is at 0(V). When the integration step is carried out with the integration time $T_1-T_2$, the integration time $T_1-T_2$ is substantially equal to $T_1$ because $T_1 \gg T_2$. Also, since $T_1 = 1/f$ (the period of the output pulse of the negative pulse generating circuit 1B being equal, of course), the following expression can be obtained:

$$V_t = K_2 \int_{t_1}^{t_2} K_1 f dt \, (t_1 = 0, t_2 = T_1 = 1/f)$$

$$= K_1 K_2 f[t]_0^{1/f}$$

$$= K_1 K_2$$

Thus, the output $V_t$ of the integrating circuit 1A has a certain value which is independent of the output frequency of the Schmitt trigger circuit 4, that is, the vocal cord vibration frequency f. As is apparent from the above description, the minimum and maximum values of the saw tooth wave, part (e), are independent of the vocal cord vibration frequency f. Stated differently, even if the vocal cord vibration frequency f is varied during the utterance, the maximum and minimum values will be maintained constant.

The light emission of the discharge tube will now be described. This takes place in a desired phase of the vocal cord vibration or in a phase which changes automatically and continuously with respect to the vocal cord vibration, by using the output of the saw tooth wave generating circuit 6. That is, the saw tooth wave shown in the part (e) of FIG. 2 and the output of the reference voltage generating circuit 9 whose output voltage is variable may be used or the output of the reference voltage automatic sweep circuit 10 whose output voltage is automatically varied.

First, the case where the discharge tube is allowed to emit light in a desired phase of the vocal cord vibration by using the instantaneous voltage of the saw tooth wave (FIG. 2, (e)) and the output of the reference voltage generating circuit 9 will be described.

In this embodiment, a variable voltage provided by a variable resistor $RL_1$ as shown in the block 9 in FIG. 7 is employed as the output of the reference voltage generating circuit 9. This output voltage can be varied by operating the variable resistor $RL_1$ by a hand or foot operated mechanism or an electric motor. The output of the saw tooth wave generating circuit 6 is applied to the comparator circuit 1D, and then the output $V_{ref1}$ of the reference voltage generating circuit 9 is applied, as a comparison voltage, to the comparator circuit 8. The instantaneous voltage of the saw tooth wave shown in FIG. 2(e) is compared with the output of the reference voltage generating circuit 9.

The output of the comparator circuit 1D is raised to a logical high level when the output of the reference voltage generating circuit 9 is equal to the saw tooth wave voltage, and it is set to a logical low level when the saw tooth wave is reset, that is, the integrating circuit 1A is reset. In this connection, one example of the output of the comparator circuit 1D obtained when the output $V_{ref1}$ is set to a certain value as indicated in the saw tooth wave (e) is as indicated in FIG. 2(f). A positive pulse having a short pulse width is formed by the monostable multivibrator 7 when the output of the comparator circuit 1D rises.

This positive pulse thus formed is employed as the discharge tube light emission control signal. One example is shown in FIG. 2(g). That is, the discharge tube light emission control signal is the output of the discharge tube light emission control signal generating circuit comprising the comparator circuit 1D and the mono-stable multivibrator 7. This signal is subjected to high voltage amplification in the high voltage amplifier circuit 11 with the frequency and synchronous position maintained unchanged as shown in FIG. 2(h). The resulting signal is applied as a trigger pulse to the discharge tube 12 to cause the latter to emit light.

As is clear from the above description, the instantaneous voltage of the saw tooth wave which is synchronous with and equal in frequency to the vocal cord vibration is compared with the output of the reference voltage generating circuit 9. The output voltage of the reference voltage generating circuit 9 is varied within the range of from the minimum value to the maximum value of the saw tooth wave voltage. As a result, the discharge tube light emission control signal can be provided in the desired phase of the vocal cord vibration and in that same phase the discharge tube is actuated to emit light. In this case, since the frequency of the saw tooth wave shown in FIG. 2(e) is equal to the frequency of the vocal cord vibration, the phase shift range is $2\pi$. More importantly, the discharge tube light emission control signal can be provided for each period of the vocal cord vibration because of the equal frequencies.

Secondly, the saw tooth wave is synchronous with the vocal cord vibration and is equal in frequency to the vocal cord vibration and its voltage maximum and minimum values are constant irrespective of the vocal cord vibration frequency. Therefore, the range of the output of the reference voltage generating circuit 9 can be held constant independent of the vocal cord vibration frequency. Accordingly, even if the vocal cord vibration frequency is varied, the amount of the phase shift obtained when the discharge tube light emission control signal for the vocal cord vibration is provided is maintained equal with respect to the same amount of variation of the output of the reference voltage generating circuit 9. The phase shift range is constant independent of the vocal cord vibration frequency.

Now, the case where the discharge tube emits light in a phase which changes automatically and continuously with respect to the vocal cord vibration by utilizing the saw tooth wave and the output of the reference voltage automatic sweep circuit 10, will be described.

In FIG. 7, reference numeral 10 designates an example of the reference voltage automatic sweep circuit. This circuit includes an integrating circuit 18, a reset circuit 19, a comparator circuit 20, and a mono-stable multivibrator 21. This example of the reference voltage automatic sweep circuit 10 shown in FIG. 7 is a saw tooth wave generating circuit well known in the art. When the output of the integrating circuit 18 becomes equal to a voltage set by resistors $R_1$ and $R_2$, the comparator circuit 20 is actuated.

The output of the comparator circuit 20 operates the mono-stable multivibrator 21 to produce an output pulse. The output of the integrating circuit 18 is reset by the reset circuit 19. This operation is repeatedly carried out in the reference voltage automatic sweep circuit 10. In this example, the repetitive time can be varied by means of a variable resistor $RL_2$ which is operated by a hand or foot-operated mechanism.

Referring back to FIG. 1, first the change-over switch 13 is operated so that instead of the output of the reference voltage generating circuit 9, the output of the reference voltage automatic sweep circuit 10 is compared with the instantaneous voltage of the output of the saw tooth wave generating circuit 6. The output of the comparator circuit 1D is applied to the mono-stable multivibrator circuit 7 to provide the discharge tube light emission control signal. This control signal is subjected to high voltage amplification in the high voltage amplifier circuit 11 and is then applied, as a trigger pulse, to the discharge tube 12 to cause the latter 12 to emit light. These steps are identical to those in the above-described case using the output of the reference voltage generating circuit 9.

This state is as shown in FIG. 3. FIG. 3(a) shows one example of the vocal cord vibration waveform similar to that in FIG. 2(a). Waveform (b) is the output of the filter circuit block 3 similar to that in FIG. 2(b). Similarly, the output of the Schmitt trigger circuit 4 is similar to that in FIG. 2(c). Waveform (d), the output of the negative pulse generating circuit 1B is also similar to that in FIG. 2(d) and waveform (e), the output of the saw tooth wave 6 is similar to that in FIG. 2(e). Waveform (f) is one example of the output of the comparator circuit 1D obtained when the output $V_{ref.2}$ of the reference voltage automatic sweep circuit 10 is changed as indicated in FIG. 3(e). Waveform (g) is the output of the mono-stable multivibrator circuit 7 when the output $V_{ref.2}$ is changed, i.e. the output of the discharge tube light emission signal generating circuit 8. Finally FIG. 3(h) is the output of the high voltage amplifier circuit 11.

More specifically, if the output of the reference voltage automatic sweep circuit 10 is automatically and continuously changed in the range from the minimum value to the maximum value of the voltage of the output e of the saw tooth wave generating circuit 6 and with a suitable repetitive time (several seconds being preferable), then the discharge tube light emission control signal is provided in a phase which changes automatically and continuously with respect to vocal cord vibration. Since the frequency of the saw tooth wave e is equal to the vocal cord vibration frequency, the phase shift range is $2\pi$. Even after the phase has been changed within this phase shift range, the same state is repeated with the phase shift range $2\pi$. That is, the state of one vocal cord vibration can be observed being moved slowly, and thereafter the same state is repeated. In this connection, as in the case employing the output of the reference voltage generating circuit 9, the discharge tube light emission control signal is provided for every period of the vocal cord vibration waveform.

It is apparent that since the saw tooth wave in FIG. 3(e) is synchronous and of equal frequency to the vocal cord vibration and its voltage minimum and maximum values are constant independently of the vocal cord vibration frequency, the variation range of the output of the reference voltage automatic sweep circuit 10 can also be constant. It is independent of the vocal cord vibration frequency and the phase shift range is constant irrespective of the vocal vibration frequency. Accordingly, when the output of the reference voltage automatic sweep circuit 10 is changed automatically and continuously, the phase shift rate at which the phase is changed in the phase shift range is independent of the vocal cord vibration frequency.

The case where the output frequency of the saw tooth wave generating circuit 6 is equal to the vocal cord vibration frequency, the phase shift range is $2\pi$ with respect to the vocal cord vibration, and the discharge tube light emission control signal is provided every period of the vocal cord vibration has been described. If it is desired to observe the vocal cords with a wider phase shift range, the following procedure is utilized.

Instead of applying the output of the Schmitt trigger circuit 4 directly to the negative pulse generating circuit 1B (FIG. 1), the square wave output of the Schmitt trigger circuit 4 is subjected to $1/(n+1)$ frequency division in a frequency divider circuit. The square wave output of the frequency divider circuit is applied to the negative pulse generating circuit 1B. In this case, the output of the saw tooth wave generating circuit 6 is in synchronization with the vocal cord vibration and its frequency becomes $1/(n+1)$ of the vocal cord vibration frequency. In addition, the minimum and maximum values of the output voltage of the saw tooth wave generating circuit 6 are constant independent of the vocal cord vibration frequency. This can be demonstrated in the case where the output frequency of the saw tooth wave generating circuit 6 is equal to the vocal cord vibration frequency because only the integration time of the integrating circuit 1A is different. The output of the saw tooth wave generating circuit 6 and the output of the reference voltage generating circuit 9 or the reference voltage automatic sweep circuit 10 is used. The discharge tube light emission control signal can be provided to allow the light emission of the discharge tube in a desired phase of the vocal cord vibration or in a phase which changes automatically and continuously with respect to the vocal cord vibration. The phase shift range with respect to the vocal cord vibration is $2(n+1)\pi$.

As in the case where the output frequency of the saw tooth wave generating circuit 6 is equal to the vocal cord vibration frequency, neither the phase shift range nor phase shift range depend on the vocal cord vibration frequency. However, in this case, the discharge tube light emission control signal is generated every $(n+1)$ periods of the vocal cord vibration waveform, because the output frequency of the saw tooth wave generating circuit 6 is $1/(n+1)$ of the vocal cord vibration frequency.

As is clear from the above description, in order to provide the discharge tube light emission control signal every period of the vocal cord vibration, it is necessary that the output frequency of the saw tooth wave generating circuit 6 equal to the vocal cord vibration frequency. In this case, the phase shift range with respect to the vocal cord vibration is necessarily $2\pi$, and the state of one vocal cord vibration can be observed. However, this can also be achieved by adding circuits to the circuitry shown in FIG. 1. Additionally, the discharge tube light emission control signal is produced every period of the vocal cord vibration and the state of $(n+1)$ vocal cord vibrations can be observed, or the phase shift range with respect to the vocal cord vibration is changed to $2(n+1)\pi$. A modification of the circuitry shown in FIG. 1 is shown in FIG. 4, in which those components which have been previously described with reference to FIG. 1 have therefore been similarly numbered. In FIG. 4, reference numeral 14 designates a polyphase pulse generating circuit and reference characters 2A and $(n+1)$A are integrating circuits similar to the integrating circuit 1A.

Reference characters 2B and $(n+1)$B, are negative pulse generating circuits similar to the negative pulse generating circuit 1B. Reference numeral 15 defines the components forming a saw tooth wave generating circuit made up of the F-V converter circuit 5, $(n+1)$ integrating circuits (1A, 2A, . . . , and $(n+1)$A), $(n+1)$ negative pulse generating circuits (1B, 2B, . . . , and $(n+1)$B) and the polyphase generating circuit 14. Reference characters 2D and $(n+1)$D are comparator circuits similar to the comparator circuit 1D and reference numeral 16 is a pulse composing circuit. Reference numeral 17 defines the discharge tube light emission control signal generating circuit comprising $(n+1)$ comparator circuits (1D, 2D, . . . , $(n+1)$D) and the pulse composing circuit 16.

In FIG. 1, the output of the F-V converter circuit 5 is applied to the integrating circuit 1A and the integrating circuit 1A is reset by the output of the negative pulse generating circuit 1B to provide the saw tooth wave. The instantaneous voltage of the saw tooth wave is compared with the output voltage of the reference voltage generating circuit 9 or the reference voltage automatic sweep circuit 10 in the comparator circuit 1D. This circuitry is arranged in parallel as shown in FIG. 4.

In addition, the circuitry in FIG. 4 is different from that in FIG. 1 in the following points: (1) The output of the Schmitt trigger circuit 4 is applied through the polyphase pulse generating circuit 14 to the reset circuits 1B, 2B, ..., (n+1)B; (2) The outputs of the comparator circuits 1D, 2D, ..., (n+1)D are applied to the pulse composing circuit 16, where positive pulses short in pulse width are produced with the rises of the outputs of the comparator circuits. These are subjected to logical summation to provide an output pulse as the output of the pulse composing circuit 16, the output pulse being applied to the high voltage amplifier circuit 11.

The polyphase pulse generating circuit 14 has (n+1) output terminals where on square wave is provided every (n+1) periods of the output of the Schmitt trigger circuit 4. These outputs 1P, 2P, ..., (n+1)P are shifted in time by one period of the output waveform of the Schmitt trigger circuit 4, as shown in FIG. 5.

Figure 9:
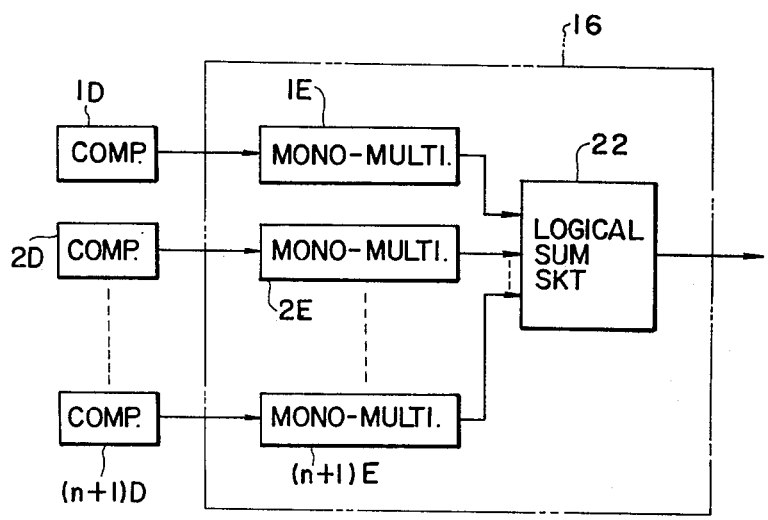
FIG. 9 is a block diagram showing the circuitry of one example of a pulse composing circuit 16 shown in FIG. 4.

FIG. 9 is a block diagram showing the circuitry of one example of a pulse composing circuit 16 shown in FIG. 4. The pulse composing circuit 16 comprises monostable multivibrator 1E, 2E, ..., (n+1)E and a logical sum circuit 22, wherein the output terminals of the comparator circuits 1D, 2D, ..., (n+1)D are connected to the input terminals of the monostable multivibrator circuits 1E, 2E, ..., (n+1)E, respectively. The output terminals of the monostable multivibrator circuits 1E, 2E, ..., (n+1)E are connected to the logical circuit 22. The output terminal of the logical sum circuit 22 is connected to the high voltage amplifier 11.

In FIG. 5, waveform (1T) shows the output of the Schmitt trigger circuit and waveform (2T) is the output 1P of the polyphase pulse generating circuit 14. Waveform (3T) is the output 2P of the polyphase pulse generating circuit 14 and (4T) is the output 3P of the polyphase pulse generating circuit 14. Finally, waveform (5T) is the output (n+1)P of the polyphase pulse generating circuit 14. These square wave outputs 1P, 2P, ..., (n+1)P of the polyphase pulse generating circuit 14 are applied to the negative pulse generating circuits 1B, 2B, ..., (n+1)B, respectively, so that the saw tooth wave outputs are provided by the integrating circuits 1A, 2A, ..., (n+1)A. The output voltages are equal in minimum and maximum values, and the values are constant independent of the vocal cord input period and amplitude.

The saw tooth waves are shifted in time successively by one period of the Schmitt trigger circuit 4. In other words, (n+1) saw tooth waves can be obtained and the rising points are shifted by 0, $2\pi$, $4\pi$, ..., $2n\pi$, respectively, with the vocal cord vibration as the reference. The instantaneous voltages of the outputs of the integrating circuits 1A through (n+1)A are compared with the output of the reference voltage generating circuit 9 or the reference voltage automatic sweep circuit 10 in the comparator circuits 1D through (n+1)D, respectively.

The outputs of the comparator circuits 1D through (n+1)D are applied to the pulse comprising circuit 16, which generates an output to the discharge tube light emission control signal every period of the vocal cord vibration. This control signal is applied to the high voltage amplifier circuit 11, where it is subjected to high voltage amplification. The resulting signal is applied, as a trigger pulse, to the discharge tube 12 to cause the latter 12 to emit light.

Hence, in the case of utilizing the output of the reference voltage generating circuit 9, the discharge voltage light emission control signal is provided in the same desired phase every period of the vocal cord vibration. In the case of utilizing the output of the reference voltage automatic sweep circuit 10, the discharge voltage light emission control signal is produced in the phase which changes automatically and continuously with respect to the vocal cord vibration, every period of the same. In this connection, as in the circuit in FIG. 1, the output of the reference voltage generating circuit 9 or the reference voltage automatic sweep circuit 10 is changed in the range of the minimum value to the maximum value of the output of each of the integrating circuits 1A through (n+1)A. Since the output frequency of each of the integrating circuits 1A through (n+1)A is 1/(n+1) of the vocal cord vibration frequency, the phase shift range with respect to the vocal cord vibration is $2(n+1)\pi$. Therefore, the state of (n+1) vocal cord vibrations can be observed. Furthermore, similarly as in the case of FIG. 1, since the minimum and maximum values of the output voltage of each of the integrating circuits 1A through (n+1)A are constant independently of the vocal cord vibration frequency, the phase shift range and the phase shift rate with respect to the vocal cord vibration are not dependent on the vocal cord vibration frequency.

Figure 6:
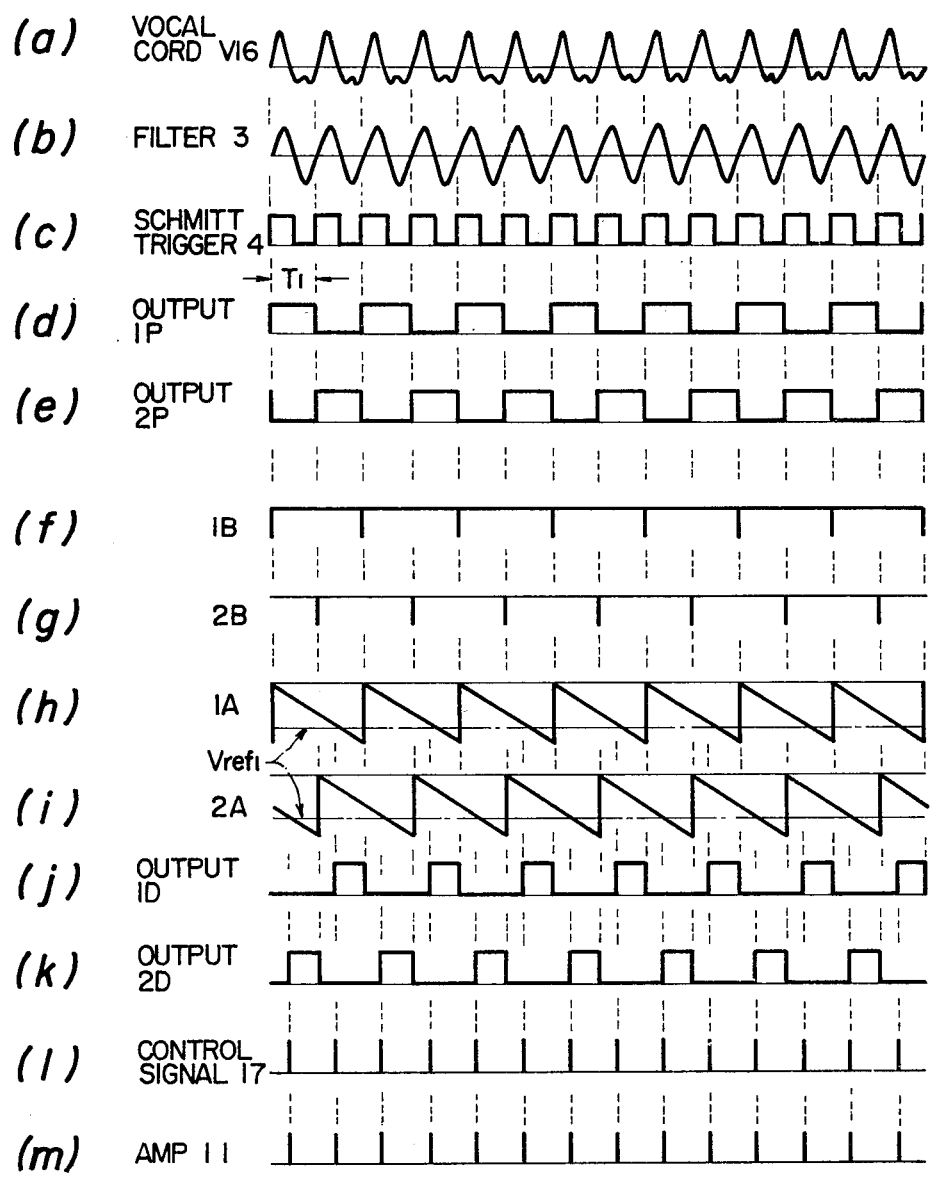
FIG. 6 (comprising a-m) is a diagram showing one example of waveforms at various parts in the circuitry shown in FIG. 4.
Figure 8:
FIG. 8 shows one example of the output waveform of the saw tooth wave generating circuit.

The waveforms at various parts in the circuitry of FIG. 4 are indicated in FIG. 6, with n=1 for instance. FIG. 6(A) shows one example of a vocal cord vibration waveform similar to that in FIG. 2(a). The output of the filter circuit block 3 similar to that in FIG. 2(b) is shown as waveform 6(B). Part (C) is the output of the Schmitt trigger circuit 4 similar to that in FIG. 2(c). Waveform (D) is the output 1P of the polyphase pulse generating circuit 14 and the part (E) is the output 2P of the circuit 14. FIG. 6(F) is the output of the negative pulse generating circuit 1B. FIG. 6(G) is the output of the negative pulse generating circuit 2B and waveform (H), the output of the integrating circuit 1A. Part(I) is the output of the integrating circuit 2A.

Furthermore, in FIG. 6, waveform (J) shows the output of the comparator circuit 1D, and part (K) is the output of the comparator circuit 2D, each being one example with the output $V_{ref.1}$ set to a certain value as shown in the parts (H) and (I). The output of the pulse composing circuit 16, that is, the output of the discharge tube light emission control signal generating circuit 17 in this case is shown in the part (L) of FIG. 6, and the output of the high voltage amplifier circuit 11 is illustrated in the part (M) of FIG. 6.

As is apparent from the wave forms of FIG. 6, the discharge tube emits light in a desired phase within the phase shift range $4\pi$. In FIG. 6, the output $V_{ref.1}$ of the reference voltage generating circuit 9 is set to a certain value. However, it is obvious that since the case of utilizing the output of the reference voltage automatic sweep circuit 10 corresponds to the case where the voltage $V_{ref.1}$ is changed automatically and continuously, the discharge tube emits light in the phase which changes automatically and continuously with respect to the vocal cord vibration.

In all of the above descriptions, the output of each of the integrating circuits 1A through (n+1)A is the saw tooth wave in which the absolute value of the voltage going from 0(V) to negative is increased. However, the case exists where the same DC bias voltage is applied to each of the saw tooth waves, where all of the saw tooth waves are inverted into saw tooth waves in which the voltage is increased from 0(V) to positive, and where the same DC bias is applied to each of the saw tooth waves thus inverted. If the output of the reference voltage generating circuit 9 or the reference voltage automatic sweep circuit 10 is changed in the range of from the minimum value to the maximum value of the voltage of each saw tooth wave, then the same effects as described above can be obtained.

As is apparent from the above description, in this invention, the minimum and maximum values of the output voltage of each of the integrating circuits 1A through (n+1)A are constant independent of the vocal cord vibration frequency. The output of the reference voltage generating circuit 9 or the reference voltage automatic sweep circuit 10 whose output voltage is changed in the range of from the minimum value to the maximum value is not dependent on the vocal cord vibration frequency and can be within a certain range. Therefore, independent of the vocal cord vibration frequency, it is possible to detect the phase of the vocal cord vibration waveform obtained when the xenon discharge tube is caused to emit light by the output voltage of the reference voltage generating circuit 9 or the output voltage of the reference voltage automatic sweep circuit 10.

While this invention has been described with respect to the preferred embodiments it is apparent that modifications may be made without departing from the essential scope of the invention.

We claim:

1. A larynx stroboscope comprising; saw tooth wave generating means for generating in synchronization with vocal cord vibrations at least one saw tooth wave; a reference voltage generating circuit having a variable output voltage; and a discharge tube light emission control signal generating circuit for generating a discharge tube light emission control signal in a phase shift range with respect to said vocal cord vibrations by comparing the instantaneous voltage of said saw tooth wave with the output of said reference voltage generating circuit, said discharge tube light emission control signal being generated in a desired phase of said vocal cord vibration over a predetermined repetition rate period of said vocal cord vibrations.

2. The larynx stroboscope of claim 1 wherein the voltage levels of each saw tooth wave in said wave train are constant in maximum and minimum values.

3. The larynx stroboscope of claims 1 or 2 wherein the discharge tube light emission control signal is generated once for every period of said vocal cord vibrations.

4. The larynx stroboscope of claims 1 or 2 wherein the discharge tube light emission control signal is generated once for a multiple number of periods of vocal cord vibration.

5. The stroboscope of claim 1, wherein said saw tooth wave generating means generates in synchronization with said vocal cord vibration one saw tooth wave having a frequency equal to the frequency of said vocal cord vibration and voltage minimum and maximum values that are constant and said discharge tube light emission control signal generating circuit generates a discharge tube light emission control signal in a desired phase in one period of said vocal cord vibration every period of said vocal cord vibration by comparing the instantaneous voltage of said one saw tooth wave with the output of said reference voltage generating circuit.

6. The stroboscope of claim 1, wherein said saw tooth wave generating means generates in synchronization with said vocal cord vibration one saw tooth wave whose frequency is $1/(n+1)$ of the frequency of said vocal cord vibration, n being equal an integer and voltage minimum and maximum values that are constant; and said discharge tube light emission control signal generating circuit generates a discharge tube light emission control signal in a desired phase of said vocal cord vibration within a phase shift range of $2(n+1)\pi$ with respect to said vocal cord vibration every $(n+1)$ period of said vocal cord vibration by comparing the instantaneous voltage of said one saw tooth wave with the output of said reference voltage generating circuit.

7. The stroboscope of claim 1, wherein said saw tooth wave generating means generates in synchronization with said vocal cord vibration $(n+1)$ saw tooth waves, the frequency of each saw tooth wave being $1/(n+1)$ of the frequency of said vocal cord vibration, the minimum and maximum values of the voltage of each saw tooth wave being constant, the points of positive slope of said saw tooth waves being delayed by $0, 2\pi, 4\pi, \ldots, $ and $2n\pi$ with said vocal cord vibration as a reference, respectively and where n is an integer; and said discharge tube light emission control signal generating circuit generates a discharge tube light emission control signal in a desired phase of said vocal cord vibration within a phase shift range of $2(n+1)$ with respect to said vocal cord vibration every period of said vocal cord vibration by comparing the instantaneous voltage of each saw tooth wave with the output of said reference voltage generating circuit.

8. A larynx stroboscope device comprising: a saw tooth generating circuit for generating in synchronization with a vocal cord vibration at least one saw tooth wave; a reference voltage automatic sweep circuit having an output voltage changed automatically and continuously; and a discharge tube light emission control signal generating circuit for comparing the instantaneous voltage of each saw tooth wave with the output of said reference voltage automatic sweep circuit to generate a discharge tube light emission control signal in a phase shift range with respect to said vocal cord vibration, said discharge tube light emission control signal being generated over a predetermined repetition rate period of said vocal cord vibration.

9. The larynx stroboscope of claim 8 wherein the voltage levels of each saw tooth wave in said wave train are constant in maximum and minimum values.

10. The larynx stroboscope of claims 8 or 9 wherein the discharge tube light emission control signal is generated once for every period of said vocal cord vibrations.

11. The larynx stroboscope of claims 8 or 9 wherein the discharge tube light emission control signal is generated once for a multiple number of periods of vocal cord vibration.

12. The larynx stroboscope as claimed in claim 8, wherein said saw tooth wave generating means generates in synchronization with said vocal cord vibration one saw tooth wave having frequency equal to the frequency of said vocal cord vibration and voltage minimum and maximum values that are constant and said discharge tube light emission control signal generating circuit generates a discharge tube light emission control signal every period of said vocal cord vibration by comparing the instantaneous voltage of said one saw tooth wave with the output of said reference voltage automatic sweep circuit.

13. The larynx stroboscope device as claimed in claim 8, wherein said saw tooth wave generating means generates in synchronization with said vocal cord vibration one saw tooth wave whose frequency is 1/(n+1) of the frequency of said vocal cord vibration wherein n is an integer and voltage minimum and maximum values are constant; said discharge tube light emission control signal generating circuit generates a discharge tube light emission control signal every (n+1) periods of said vocal cord vibration by comparing the instantaneous voltage of said one saw tooth wave with the output of said reference voltage automatic sweep circuit.

14. The larynx stroboscope device as claimed in claim 8, wherein said saw tooth wave generating means generates in synchronization with said vocal cord vibration (n+1) saw tooth waves, the frequency of each saw tooth wave being 1/(n+1) of the frequency of said vocal cord vibration, the minimum and maximum values of the voltage of each saw tooth wave being constant, the points of positive slope of said saw tooth waves being delayed by $0, 2\pi, 4\pi, \ldots, 2n\pi$ with said vocal cord vibration as a reference, respectively, where n is an integer; and said discharge tube light emission control signal generating circuit generates a discharge tube light emission control signal every period of said vocal cord vibration by comparing the instantaneous voltage of each saw tooth wave with the output of said reference voltage automatic sweep circuit.

* * * * *